US012076229B2

(12) United States Patent
Ben Nun

(10) Patent No.: US 12,076,229 B2
(45) Date of Patent: *Sep. 3, 2024

(54) ACCOMMODATING INTRAOCULAR LENS ASSEMBLIES AND ACCOMMODATION MEASUREMENT IMPLANT

(71) Applicant: ForSight Vision6, Inc., Brisbane, CA (US)

(72) Inventor: Joshua Ben Nun, D.N. Vitkin (IL)

(73) Assignee: ForSight Vision6, Inc., South San Francisco, CA (US)

( * ) Notice: Subject to any disclaimer, the term of this patent is extended or adjusted under 35 U.S.C. 154(b) by 714 days.

This patent is subject to a terminal disclaimer.

(21) Appl. No.: 17/166,680

(22) Filed: Feb. 3, 2021

(65) Prior Publication Data
US 2021/0259826 A1 Aug. 26, 2021

Related U.S. Application Data

(60) Continuation of application No. 16/372,746, filed on Apr. 2, 2019, now Pat. No. 10,912,643, which is a
(Continued)

(30) Foreign Application Priority Data

Apr. 29, 2004 (IL) .......................................... 161706

(51) Int. Cl.
A61F 2/16 (2006.01)

(52) U.S. Cl.
CPC .......... A61F 2/1635 (2013.01); A61F 2/1613 (2013.01); A61F 2/1616 (2013.01);
(Continued)

(58) Field of Classification Search
None
See application file for complete search history.

(56) References Cited

U.S. PATENT DOCUMENTS 3,950,082 A 4/1976 Volk
4,122,556 A 10/1978 Poler
(Continued)

FOREIGN PATENT DOCUMENTS

CN 101137338 A 3/2008
EP 0 156 472 A1 10/1985
(Continued)

OTHER PUBLICATIONS

Chu, Ralph Y. and Buliano, Megan. Accommodating IOLS by Ralph Chu et al., Cataract & Refractive Surgery Today, May 2004. 21 pages.
(Continued)

Primary Examiner — Leslie A Lopez
(74) Attorney, Agent, or Firm — Mintz Levin Cohn Ferris Glovsky and Popeo, P.C.

(57) ABSTRACT

The present invention pertains to accommodating intraocular lens (AIOL) assemblies including a haptics system for self-anchoring implantation in a human eye's annular ciliary sulcus for retaining an AIOL at a desired position along the human eye's visual axis, and an accommodation measurement implant (AMI) for determining accommodation and accommodation forces in an experimental set-up including an animal's eye.

8 Claims, 7 Drawing Sheets

Related U.S. Application Data division of application No. 14/621,305, filed on Feb. 12, 2015, now abandoned, which is a continuation of application No. 12/906,598, filed on Oct. 18, 2010, now Pat. No. 8,956,409, which is a continuation of application No. 11/568,416, filed as application No. PCT/IL2005/000456 on May 1, 2005, now Pat. No. 7,842,087.

(60) Provisional application No. 60/589,567, filed on Jul. 21, 2004.

(52) U.S. Cl.
CPC ..... *A61F 2/1648* (2013.01); *A61F 2002/1683* (2013.01); *A61F 2002/16902* (2015.04); *A61F 2002/1699* (2015.04); *A61F 2220/0016* (2013.01)

(56) References Cited

U.S. PATENT DOCUMENTS

| | | |
|---|---|---|
| 4,159,546 A | 7/1979 | Shearing |
| 4,254,509 A | 3/1981 | Tennant |
| 4,298,994 A | 11/1981 | Clayman |
| 4,340,979 A | 7/1982 | Kelman |
| 4,373,218 A * | 2/1983 | Schachar .............. A61F 2/1627 623/6.22 |
| 4,409,690 A | 10/1983 | Gess |
| 4,409,691 A | 10/1983 | Levy |
| 4,445,998 A | 5/1984 | Kanda et al. |
| 4,446,581 A | 5/1984 | Blake |
| 4,485,498 A | 12/1984 | Gimbel |
| 4,494,254 A | 1/1985 | Lopez |
| 4,530,117 A | 7/1985 | Kelman |
| RE31,963 E | 8/1985 | Kelman |
| 4,556,998 A | 12/1985 | Siepser |
| 4,575,374 A | 3/1986 | Anis |
| 4,581,033 A | 4/1986 | Callahan |
| 4,589,147 A | 5/1986 | Nevyas |
| 4,591,358 A | 5/1986 | Kelman |
| 4,615,701 A | 10/1986 | Woods |
| 4,671,283 A | 6/1987 | Hoskin et al. |
| 4,676,794 A | 6/1987 | Kelman |
| 4,685,921 A | 8/1987 | Peyman |
| 4,731,078 A | 3/1988 | Stoy et al. |
| 4,734,095 A | 3/1988 | Siepser |
| 4,750,904 A | 6/1988 | Price, Jr. |
| 4,769,035 A | 9/1988 | Kelman |
| 4,782,820 A | 11/1988 | Woods |
| 4,787,903 A | 11/1988 | Grendahl |
| 4,808,181 A | 2/1989 | Kelman |
| 4,816,030 A | 3/1989 | Robinson |
| 4,816,031 A | 3/1989 | Pfoff |
| 4,842,601 A | 6/1989 | Smith |
| RE33,039 E | 8/1989 | Arnott |
| 4,865,601 A | 9/1989 | Caldwell et al. |
| 4,888,012 A | 12/1989 | Horn et al. |
| 4,888,016 A | 12/1989 | Langerman |
| 4,892,543 A | 1/1990 | Turley |
| 4,932,966 A | 6/1990 | Christie et al. |
| 4,932,968 A | 6/1990 | Caldwell et al. |
| 4,957,505 A | 9/1990 | McDonald |
| 4,969,897 A | 11/1990 | Kalb |
| 4,976,732 A | 12/1990 | Vorosmarthy |
| 4,990,159 A | 2/1991 | Kraff |
| 5,026,373 A | 6/1991 | Ray et al. |
| 5,066,301 A | 11/1991 | Wiley |
| 5,078,742 A | 1/1992 | Dahan |
| 5,171,266 A | 12/1992 | Wiley et al. |
| 5,171,268 A | 12/1992 | Ting et al. |
| 5,171,320 A | 12/1992 | Nishi |
| 5,176,701 A | 1/1993 | Dusek et al. |
| RE34,424 E | 10/1993 | Walman |
| 5,275,623 A | 1/1994 | Sarfarazi |
| 5,282,851 A | 2/1994 | Jacob-LaBarre |
| 5,288,293 A | 2/1994 | O'Donnell, Jr. |
| 5,336,262 A | 8/1994 | Chu |
| 5,346,502 A | 9/1994 | Estabrook et al. |
| 5,443,506 A | 8/1995 | Garabet |
| 5,476,512 A | 12/1995 | Sarfarazi |
| 5,476,514 A | 12/1995 | Cumming |
| 5,476,515 A | 12/1995 | Kelman et al. |
| 5,480,426 A | 1/1996 | Chu |
| 5,484,447 A | 1/1996 | Waldock et al. |
| 5,489,302 A * | 2/1996 | Skottun ............... A61F 2/1694 623/6.13 |
| 5,496,366 A | 3/1996 | Cumming |
| 5,522,891 A | 6/1996 | Klaas |
| 5,567,365 A | 10/1996 | Weinschenk, III et al. |
| 5,571,177 A | 11/1996 | Deacon et al. |
| 5,584,304 A | 12/1996 | Brady |
| 5,607,472 A | 3/1997 | Thompson |
| 5,628,795 A | 5/1997 | Langerman |
| 5,674,282 A | 10/1997 | Cumming |
| 5,684,637 A | 11/1997 | Floyd |
| 5,722,952 A | 3/1998 | Schachar |
| 5,752,960 A | 5/1998 | Nallakrishnan |
| 5,766,244 A | 6/1998 | Binder |
| 5,766,245 A | 6/1998 | Fedorov et al. |
| 5,774,273 A | 6/1998 | Bornhorst |
| 5,800,806 A | 9/1998 | Yamamoto |
| 5,843,188 A | 12/1998 | McDonald |
| 5,871,455 A | 2/1999 | Ueno |
| 5,895,610 A | 4/1999 | Chang et al. |
| 5,919,230 A | 7/1999 | Sambursky |
| 5,932,205 A | 8/1999 | Wang et al. |
| 5,968,094 A | 10/1999 | Werblin et al. |
| 5,984,962 A | 11/1999 | Anello et al. |
| 6,007,579 A | 12/1999 | Lipshitz et al. |
| 6,013,101 A | 1/2000 | Israel |
| 6,027,531 A | 2/2000 | Tassignon |
| 6,045,535 A | 4/2000 | Ben Nun |
| 6,051,024 A | 4/2000 | Cumming |
| 6,096,078 A | 8/2000 | McDonald |
| 6,110,202 A | 8/2000 | Barraquer et al. |
| 6,117,171 A * | 9/2000 | Skottun ............... A61F 2/1635 623/6.37 |
| 6,120,538 A | 9/2000 | Rizzo, III et al. |
| 6,129,759 A | 10/2000 | Chambers |
| 6,143,315 A | 11/2000 | Wang et al. |
| 6,164,282 A | 12/2000 | Gwon et al. |
| 6,188,526 B1 | 2/2001 | Sasaya et al. |
| 6,193,750 B1 | 2/2001 | Cumming |
| 6,197,057 B1 | 3/2001 | Peyman et al. |
| 6,197,059 B1 | 3/2001 | Cumming |
| 6,200,342 B1 | 3/2001 | Tassignon |
| 6,228,115 B1 | 5/2001 | Hoffmann et al. |
| 6,261,321 B1 | 7/2001 | Kellan |
| 6,277,146 B1 | 8/2001 | Peyman et al. |
| 6,280,469 B1 | 8/2001 | Terry et al. |
| 6,280,471 B1 | 8/2001 | Peyman et al. |
| 6,299,618 B1 | 10/2001 | Sugiura |
| 6,299,641 B1 | 10/2001 | Woods |
| 6,342,073 B1 | 1/2002 | Cumming et al. |
| 6,387,126 B1 | 5/2002 | Cumming |
| 6,406,494 B1 | 6/2002 | Laguette et al. |
| 6,423,094 B1 | 7/2002 | Sarfarazi |
| 6,443,984 B1 | 9/2002 | Jahn et al. |
| 6,443,985 B1 | 9/2002 | Woods |
| 6,450,642 B1 | 9/2002 | Jethmalani et al. |
| 6,464,725 B2 | 10/2002 | Skottun |
| 6,488,708 B2 | 12/2002 | Sarfarazi |
| 6,493,151 B2 | 12/2002 | Schachar |
| 6,494,910 B1 | 12/2002 | Ganem et al. |
| 6,494,911 B2 | 12/2002 | Cumming |
| 6,503,276 B2 | 1/2003 | Lang et al. |
| 6,506,212 B2 | 1/2003 | Zhou et al. |
| 6,520,691 B2 | 2/2003 | Nomura et al. |
| 6,524,340 B2 | 2/2003 | Israel |
| 6,552,860 B1 | 4/2003 | Alden |
| 6,554,860 B2 | 4/2003 | Hoffmann et al. |
| 6,558,420 B2 | 5/2003 | Green |
| 6,570,718 B2 | 5/2003 | Nomura et al. |

(56) References Cited

U.S. PATENT DOCUMENTS

| | | |
|---|---|---|
| 6,592,621 B1 | 7/2003 | Domino |
| 6,596,026 B1 | 7/2003 | Gross et al. |
| 6,599,317 B1 | 7/2003 | Weinschenk, III et al. |
| 6,605,093 B1 | 8/2003 | Blake |
| 6,616,692 B1 | 9/2003 | Glick et al. |
| 6,638,305 B2 | 10/2003 | Laguette |
| 6,638,306 B2 | 10/2003 | Cumming |
| 6,645,245 B1 | 11/2003 | Preussner |
| 6,645,246 B1 | 11/2003 | Weinschenk, III et al. |
| 6,730,123 B1 | 5/2004 | Klopotek |
| 6,733,122 B1 | 5/2004 | Feurer et al. |
| 6,739,722 B2 | 5/2004 | Laguette et al. |
| 6,749,634 B2 | 6/2004 | Hanna |
| 6,790,232 B1 | 9/2004 | Lang |
| 6,818,017 B1 | 11/2004 | Shu |
| 6,836,374 B2 | 12/2004 | Esch et al. |
| 6,849,091 B1 | 2/2005 | Cumming |
| 6,851,804 B2 | 2/2005 | Jethmalani et al. |
| 6,855,164 B2 | 2/2005 | Glazier |
| 6,860,601 B2 | 3/2005 | Shadduck |
| 6,930,838 B2 | 8/2005 | Schachar |
| 6,935,743 B2 | 8/2005 | Shadduck |
| 6,960,231 B2 | 11/2005 | Tran |
| 6,966,649 B2 | 11/2005 | Shadduck |
| 6,972,033 B2 | 12/2005 | McNicholas |
| 7,008,449 B2 | 3/2006 | Willis et al. |
| 7,025,783 B2 | 4/2006 | Brady et al. |
| 7,037,338 B2 | 5/2006 | Nagamoto |
| 7,060,094 B2 | 6/2006 | Shahinpoor et al. |
| 7,068,439 B2 | 6/2006 | Esch et al. |
| 7,097,660 B2 | 8/2006 | Portney |
| 7,118,596 B2 | 10/2006 | Zadno-Azizi et al. |
| 7,118,597 B2 | 10/2006 | Miller et al. |
| 7,122,053 B2 | 10/2006 | Esch |
| 7,137,994 B2 | 11/2006 | de Juan, Jr. et al. |
| 7,217,288 B2 | 5/2007 | Esch et al. |
| 7,220,279 B2 | 5/2007 | Nun |
| 7,229,476 B2 | 6/2007 | Azar |
| 7,247,168 B2 | 7/2007 | Esch et al. |
| 7,256,943 B1 | 8/2007 | Kobrin et al. |
| 7,261,737 B2 | 8/2007 | Esch et al. |
| 7,278,739 B2 | 10/2007 | Shadduck |
| 7,293,873 B2 | 11/2007 | Dai et al. |
| 7,341,599 B1 | 3/2008 | Peyman |
| 7,350,916 B2 | 4/2008 | Hong et al. |
| 7,369,321 B1 | 5/2008 | Ren et al. |
| 7,381,221 B2 | 6/2008 | Lang et al. |
| 7,384,429 B2 | 6/2008 | Hanna |
| 7,438,723 B2 | 10/2008 | Esch |
| 7,453,646 B2 | 11/2008 | Lo |
| 7,485,144 B2 | 2/2009 | Esch |
| 7,601,169 B2 | 10/2009 | Phillips |
| 7,615,056 B2 | 11/2009 | Ayton et al. |
| 7,637,947 B2 | 12/2009 | Smith et al. |
| 7,675,686 B2 | 3/2010 | Lo et al. |
| 7,763,069 B2 | 7/2010 | Brady et al. |
| 7,776,088 B2 | 8/2010 | Shadduck |
| 7,815,678 B2 | 10/2010 | Ben Nun |
| 7,842,087 B2 | 11/2010 | Ben Nun |
| 7,854,764 B2 | 12/2010 | Ben Nun |
| 7,883,540 B2 | 2/2011 | Niwa et al. |
| 7,976,520 B2 | 7/2011 | Nun |
| 7,985,253 B2 | 7/2011 | Cumming |
| 7,988,285 B2 | 8/2011 | Sandstedt et al. |
| 7,998,199 B2 | 8/2011 | Ben Nun |
| 8,018,658 B2 | 9/2011 | Lo |
| 8,034,106 B2 | 10/2011 | Mentak et al. |
| 8,038,711 B2 | 10/2011 | Clarke |
| 8,048,156 B2 | 11/2011 | Geraghty et al. |
| 8,158,712 B2 | 4/2012 | Your |
| 8,314,927 B2 | 11/2012 | Choi et al. |
| 8,343,216 B2 | 1/2013 | Brady et al. |
| 8,377,125 B2 | 2/2013 | Kellan |
| 8,414,646 B2 | 4/2013 | De Juan, Jr. et al. |
| 8,663,235 B2 | 3/2014 | Tassignon |
| 8,668,734 B2 | 3/2014 | Hildebrand et al. |
| 8,851,670 B2 | 10/2014 | Dai et al. |
| 8,900,298 B2 | 12/2014 | Anvar et al. |
| 8,956,408 B2 | 2/2015 | Smiley et al. |
| 8,968,396 B2 | 3/2015 | Matthews et al. |
| 8,974,526 B2 | 3/2015 | Bogaert |
| 9,005,282 B2 | 4/2015 | Chang et al. |
| 9,044,317 B2 | 6/2015 | Hildebrand et al. |
| 9,114,005 B2 | 8/2015 | Simonov et al. |
| 9,326,846 B2 | 5/2016 | Devita Gerardi et al. |
| 9,421,089 B2 | 8/2016 | Zadno-Azizi |
| 9,681,981 B2 | 6/2017 | Stevens |
| 9,782,291 B2 | 10/2017 | Stevens |
| 9,814,568 B2 | 11/2017 | Ben Nun |
| 10,166,096 B2 | 1/2019 | Ben Nun |
| 2001/0001836 A1 | 5/2001 | Cumming |
| 2002/0103535 A1 | 8/2002 | Portney |
| 2002/0103537 A1 | 8/2002 | Willis et al. |
| 2002/0188351 A1 | 12/2002 | Laguette |
| 2003/0060878 A1 | 3/2003 | Shadduck |
| 2003/0060881 A1 | 3/2003 | Glick et al. |
| 2003/0097177 A1 | 5/2003 | Tran |
| 2003/0109926 A1 | 6/2003 | Portney |
| 2003/0149480 A1 | 8/2003 | Shadduck |
| 2003/0171809 A1 | 9/2003 | Phillips |
| 2003/0187504 A1 | 10/2003 | Weinschenk et al. |
| 2004/0006387 A1 | 1/2004 | Kelman |
| 2004/0015140 A1 | 1/2004 | Shields |
| 2004/0034417 A1 | 2/2004 | Heyman |
| 2004/0039446 A1 | 2/2004 | McNicholas |
| 2004/0073304 A1 | 4/2004 | Weinschenk et al. |
| 2004/0082993 A1 | 4/2004 | Woods |
| 2004/0082995 A1 | 4/2004 | Woods |
| 2004/0111153 A1 | 6/2004 | Woods et al. |
| 2004/0148022 A1 | 7/2004 | Eggleston |
| 2004/0148023 A1 | 7/2004 | Shu |
| 2004/0162612 A1 | 8/2004 | Portney et al. |
| 2004/0169816 A1* | 9/2004 | Esch ............ A61F 2/1624 351/159.02 |
| 2004/0169820 A1 | 9/2004 | Dai et al. |
| 2004/0181279 A1 | 9/2004 | Nun |
| 2004/0237971 A1 | 12/2004 | Radhakrishnan et al. |
| 2005/0015143 A1 | 1/2005 | Willis et al. |
| 2005/0021138 A1 | 1/2005 | Woods |
| 2005/0060032 A1 | 3/2005 | Magnante et al. |
| 2005/0065534 A1 | 3/2005 | Hohl |
| 2005/0090896 A1 | 4/2005 | Ben Nun |
| 2005/0107873 A1 | 5/2005 | Zhou |
| 2005/0113914 A1 | 5/2005 | Miller et al. |
| 2005/0119740 A1* | 6/2005 | Esch ............ A61F 2/1635 623/6.37 |
| 2005/0125059 A1 | 6/2005 | Pinchuk et al. |
| 2005/0137703 A1 | 6/2005 | Chen |
| 2005/0177229 A1 | 8/2005 | Boxer Wachler |
| 2005/0251253 A1 | 11/2005 | Gross |
| 2006/0047340 A1 | 3/2006 | Brown |
| 2006/0064162 A1 | 3/2006 | Klima |
| 2006/0069431 A1 | 3/2006 | Graney et al. |
| 2006/0069433 A1 | 3/2006 | Nun |
| 2006/0074487 A1 | 4/2006 | Gilg |
| 2006/0100701 A1 | 5/2006 | Esch et al. |
| 2006/0134173 A1 | 6/2006 | Liu et al. |
| 2006/0238702 A1 | 10/2006 | Glick et al. |
| 2006/0259138 A1 | 11/2006 | Peyman |
| 2007/0010881 A1 | 1/2007 | Soye et al. |
| 2007/0027538 A1 | 2/2007 | Aharoni et al. |
| 2007/0027541 A1 | 2/2007 | Aharoni et al. |
| 2007/0054131 A1 | 3/2007 | Stewart |
| 2007/0078515 A1 | 4/2007 | Brady |
| 2007/0088433 A1 | 4/2007 | Esch et al. |
| 2007/0093891 A1 | 4/2007 | Tabernero et al. |
| 2007/0123981 A1 | 5/2007 | Tassignon |
| 2007/0123982 A1 | 5/2007 | Yablonski et al. |
| 2007/0129798 A1 | 6/2007 | Chawdhary |
| 2007/0129799 A1 | 6/2007 | Schedler |
| 2007/0129800 A1 | 6/2007 | Cumming |
| 2007/0129801 A1 | 6/2007 | Cumming |
| 2007/0129803 A1 | 6/2007 | Cumming et al. |
| 2007/0185574 A1 | 8/2007 | Ben Nun |

(56) References Cited

U.S. PATENT DOCUMENTS

| | | |
|---|---|---|
| 2007/0244561 A1 | 10/2007 | Ben Nun |
| 2008/0004699 A1 | 1/2008 | Ben Nun |
| 2008/0046075 A1 | 2/2008 | Esch et al. |
| 2008/0046076 A1 | 2/2008 | Rombach |
| 2008/0097459 A1 | 4/2008 | Kammerlander et al. |
| 2008/0106698 A1 | 5/2008 | Dai et al. |
| 2008/0119864 A1 | 5/2008 | Deinzer et al. |
| 2008/0125862 A1 | 5/2008 | Blake |
| 2008/0129962 A1 | 6/2008 | Dai et al. |
| 2008/0188930 A1 | 8/2008 | Mentak et al. |
| 2008/0300680 A1 | 12/2008 | Joshua |
| 2009/0171458 A1 | 7/2009 | Kellan et al. |
| 2009/0198247 A1 | 8/2009 | Ben Nun |
| 2009/0264998 A1 | 10/2009 | Mentak et al. |
| 2010/0121444 A1 | 5/2010 | Ben Nun |
| 2011/0118834 A1 | 5/2011 | Lo et al. |
| 2012/0078364 A1 | 3/2012 | Stenger |
| 2013/0013061 A1 | 1/2013 | Coroneo |
| 2013/0110235 A1 | 5/2013 | Schwiegerling |
| 2013/0116781 A1 | 5/2013 | Ben Nun |
| 2013/0245754 A1 | 9/2013 | Blum et al. |
| 2014/0121768 A1 | 5/2014 | Simpson |
| 2015/0250584 A1 | 9/2015 | Blum et al. |
| 2015/0257874 A1 | 9/2015 | Hildebrand et al. |
| 2019/0183637 A1 | 6/2019 | Ben Nun |
| 2021/0290372 A1 | 9/2021 | Ben Nun |

FOREIGN PATENT DOCUMENTS

| | | |
|---|---|---|
| EP | 0 162 573 A2 | 11/1985 |
| EP | 637503 A1 | 2/1995 |
| EP | 1 321 112 A1 | 6/2003 |
| FR | 2 794 965 A1 | 12/2000 |
| JP | 2001525220 A | 12/2001 |
| JP | 2005007029 A | 1/2005 |
| JP | 2005533611 A | 11/2005 |
| JP | 2008-532617 A | 8/2008 |
| JP | 2008183434 A | 8/2008 |
| JP | 2009532176 A | 9/2009 |
| TW | 523408 B | 3/2003 |
| WO | WO-83/00998 A1 | 3/1983 |
| WO | WO-93/03686 A2 | 3/1993 |
| WO | WO-94/28825 A1 | 12/1994 |
| WO | WO-95/20367 A1 | 8/1995 |
| WO | WO-98/05273 A1 | 2/1998 |
| WO | WO-98/10717 A1 | 3/1998 |
| WO | WO-99/29266 A1 | 6/1999 |
| WO | WO-99/62434 A1 | 12/1999 |
| WO | WO-00/30566 A1 | 6/2000 |
| WO | WO-00/61036 A1 | 10/2000 |
| WO | WO-00/66037 A1 | 11/2000 |
| WO | WO-01/08606 A1 | 2/2001 |
| WO | WO-01/60286 A1 | 8/2001 |
| WO | WO-02/065951 A2 | 8/2002 |
| WO | WO-03/000154 A2 | 1/2003 |
| WO | WO-03/015669 A1 | 2/2003 |
| WO | WO-03/017867 A2 | 3/2003 |
| WO | WO-03/017873 A1 | 3/2003 |
| WO | WO-2004/010905 A2 | 2/2004 |
| WO | WO-2004/037122 A2 | 5/2004 |
| WO | WO-2004/037127 A2 | 5/2004 |
| WO | WO-2004/053568 A1 | 6/2004 |
| WO | WO-2004/107024 A1 | 12/2004 |
| WO | WO-2005/057272 A2 | 6/2005 |
| WO | WO-2005/082285 A1 | 9/2005 |
| WO | WO-2005/104994 A2 | 11/2005 |
| WO | WO-2006/040759 A1 | 4/2006 |
| WO | WO-2006/103674 A2 | 10/2006 |
| WO | WO-2007/048615 A1 | 5/2007 |
| WO | WO-2007/113832 A2 | 10/2007 |
| WO | WO-2007/117476 A2 | 10/2007 |
| WO | WO-2008/023379 A2 | 2/2008 |
| WO | WO-2008/031231 A1 | 3/2008 |
| WO | WO-2008/083283 A2 | 7/2008 |
| WO | WO-2008/097915 A1 | 8/2008 |
| WO | WO-2008/107882 A2 | 9/2008 |
| WO | WO-2009/122409 A1 | 10/2009 |
| WO | WO-2010/010565 A2 | 1/2010 |
| WO | WO-2012/023133 A1 | 2/2012 |

OTHER PUBLICATIONS

Gimbel, H.V., Debroff, B.M. (2004), "Intraocular lens optic capture." J Cataract Refract Surg Jan. 2004;30(1):200-6.

Notification of Transmittal of the International Preliminary Report on Patentability for PCT/IL2009/000728 filed Jul. 26, 2009 (having a priority date of Jul. 24, 2008). 19 pages.

\* cited by examiner

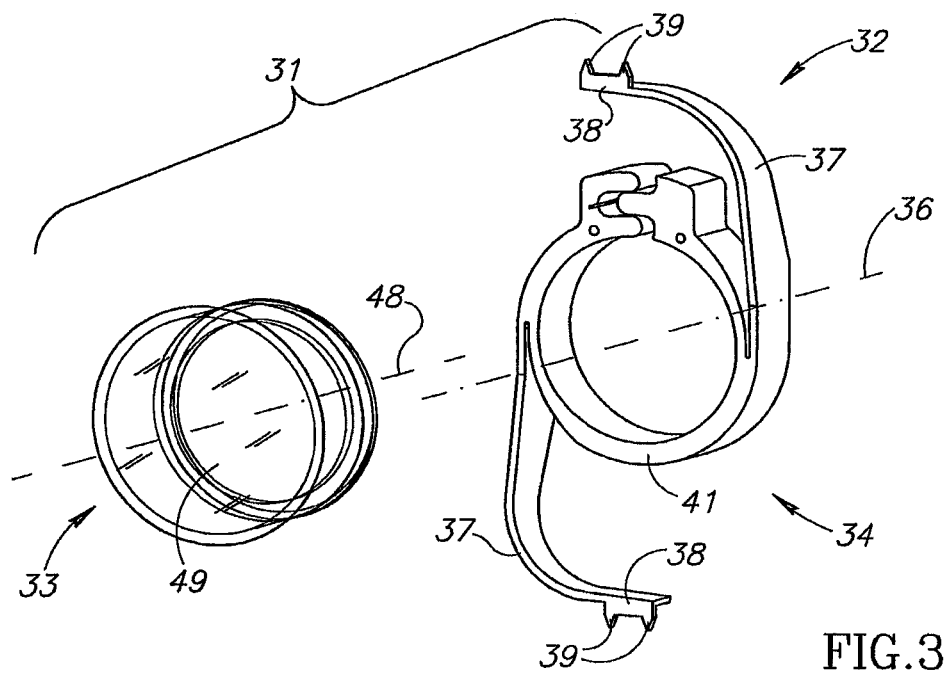
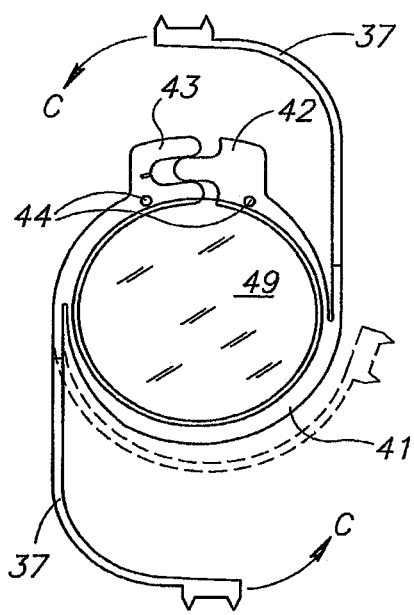
FIG.4
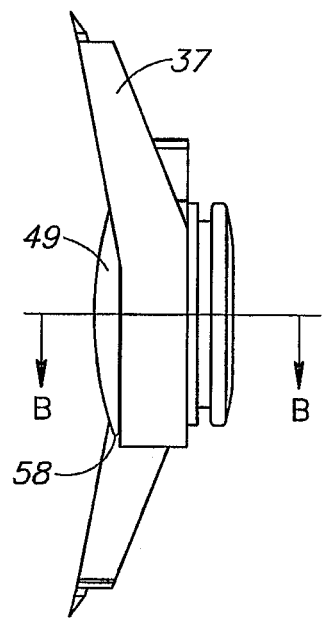
FIG.5

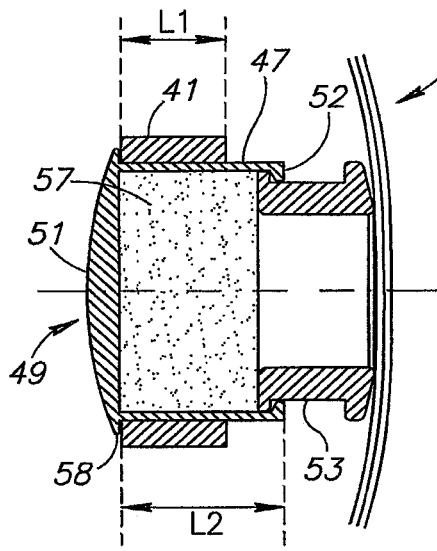
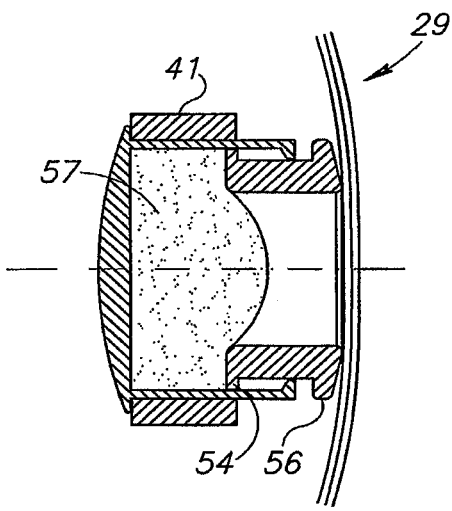
FIG.6  FIG.7
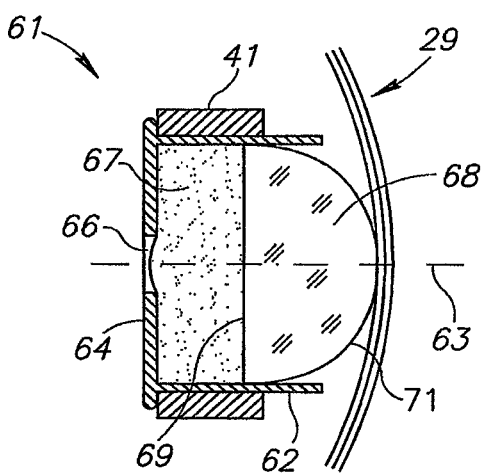
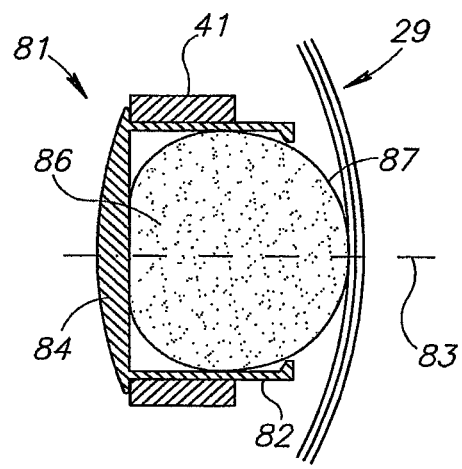
FIG.8  FIG.9

ACCOMMODATING INTRAOCULAR LENS ASSEMBLIES AND ACCOMMODATION MEASUREMENT IMPLANT

CROSS-REFERENCE TO RELATED APPLICATIONS

This application is a continuation of U.S. patent application Ser. No. 16/372,746, filed Apr. 2, 2019, which is a divisional of U.S. patent application Ser. No. 14/621,305, filed Feb. 12, 2015, now abandoned, which is a continuation of U.S. patent application Ser. No. 12/906,598, filed Oct. 18, 2010, which issued as U.S. Pat. No. 8,956,409, which is a Continuation of U.S. patent application Ser. No. 11/568,416, filed Oct. 27, 2006, which issued as U.S. Pat. No. 7,842,087 on Nov. 30, 2010, and which was a national stage application for PCT/IL2005/000456 filed May 1, 2005, claiming priority to IL 161706 filed Apr. 29, 2004 and to U.S. 60/589,567 filed Jul. 21, 2004, all of which are incorporated herein by reference in their entirety.

TECHNICAL FIELD

The invention pertains to accommodating intraocular lens assemblies and apparatus for measuring accommodation in an experimental set-up including an animal eye.

BACKGROUND OF THE INVENTION

Commonly owned PCT International Application No. PCT/IL02/00693 entitled Accommodating Lens Assembly and published under PCT International Publication No. WO 03/015669 illustrates and describes accommodating intraocular lens (hereinafter AIOL) assemblies, the contents of which are incorporated herein by reference. The AIOL assemblies include a haptics system adapted to be securely fixed in a human eye's annular ciliary sulcus at at least two spaced apart stationary anchor points so that it may act as a reference plane for an AIOL of continuously variable Diopter strength affected by a human eye's capsular diaphragm acting thereagainst from a posterior direction and under control of its sphincter-like ciliary body. The haptics system includes a rigid planar haptics plate with a telescoping haptics member for sliding extension. The haptics plate and the haptics member are preferably self-anchoring as illustrated and described in commonly owned PCT International Application No. PCT/IL02/00128 entitled Intraocular Lens and published under PCT International Publication No. WO 02/065951, the contents of which are incorporated herein by reference. However, the haptics systems are not readily foldable thereby requiring a relatively large incision for insertion of an AIOL assembly into a human eye. Still further, anterior movements of a human eye's capsular diaphragm may lead to bulging of an AIOL assembly in an anterior direction instead of affecting an AIOL's Diopter strength. Moreover, the AIOL assemblies do not afford in situ re-adjustment along a human eye's visual axis which may be required due to capsular contraction thereby requiring that a subject resort to wearing spectacles or undergoing a surgical procedure for correcting his eyesight.

U.S. Pat. No. 6,739,722 to Laguette et al. illustrates and describes apparatus for measuring accommodation of a human eye including a target, a Badal lens, and a viewing aperture where the Badal lens and the viewing aperture are positioned so that when the target moves towards or away from the lens, the apparent size of the target remains constant to a subject looking in the viewing aperture regardless of the distance the target moves.

BRIEF SUMMARY OF THE INVENTION

Generally speaking, the present invention pertains to AIOL assemblies for self-anchoring implantation in a human eye's annular ciliary sulcus at least two and preferably more spaced apart stationary anchor points and having an AIOL of variable Diopter strength capable of in situ selective displacement along the human eye's visual axis for enabling accurate eyesight correction in general, and for compensating for capsular contraction in particular. The AIOLs include at least one shape memory optical element resiliently elastically deformable between a natural shape with a first Diopter strength and a deformed shape with a second Diopter strength different than the first Diopter strength whereby the AIOL has a continuously variable Diopter strength between a minimum Diopter strength for distance vision purposes and a maximum Diopter strength for near vision purposes. The first Diopter strength can be greater than the second Diopter strength or vice versa.

The AIOL assemblies can be implemented in either a two component construction including a discrete haptics system for selectively retaining a discrete AIOL or a unitary construction including a haptics system integrally formed with an AIOL. Axial re-positioning of a two component AIOL assembly involves displacement of its AIOL relative to its haptics system which remains stationary relative to its stationary anchor points. Against that, axial re-positioning of a unitary AIOL assembly involves adjusting the position of the portion of its haptics system holding its AIOL relative to its stationary anchor points. In the latter case, this is achieved by the haptics system including haptics plastically deformable on heating to a so-called glass transmission temperature higher than a human eye's normal 36° C. temperature but sufficiently low not to damage a human eye's internal structures by irradiation with selective electromagnetic radiation.

The present invention also pertains to an accommodation measurement implant (AMI) for determining accommodation and the accommodation forces in an experimental set-up including an animal eye.

BRIEF DESCRIPTION OF THE DRAWINGS

In order to understand the invention and to see how it can be carried out in practice, preferred embodiments will now be described, by way of non-limiting examples only, with reference to the accompanying drawings in which similar parts are likewise numbered, and in which:

FIG. 3 is an exploded perspective view of a two component AIOL assembly including a discrete haptics system and a discrete natural low Diopter strength AIOL in accordance with the present invention;

FIG. 4 is an assembled front view of FIG. 3's AIOL assembly;

FIG. 5 is an assembled side view of FIG. 3's AIOL assembly;

FIG. 6 is a longitudinal cross section view of FIG. 3's AIOL in its natural extended position along line B-B in FIG. 5;

FIG. 7 is a longitudinal cross section view of FIG. 3's AIOL in a compressed position along line B-B in FIG. 5;

FIG. 8 is a longitudinal cross sectional view of another discrete natural low Diopter strength AIOL in its natural state in accordance with the present invention;

FIG. 9 is a longitudinal cross sectional view of a natural discrete high Diopter strength AIOL in its natural state in accordance with the present invention;

DETAILED DESCRIPTION OF THE INVENTION

Figure 1:
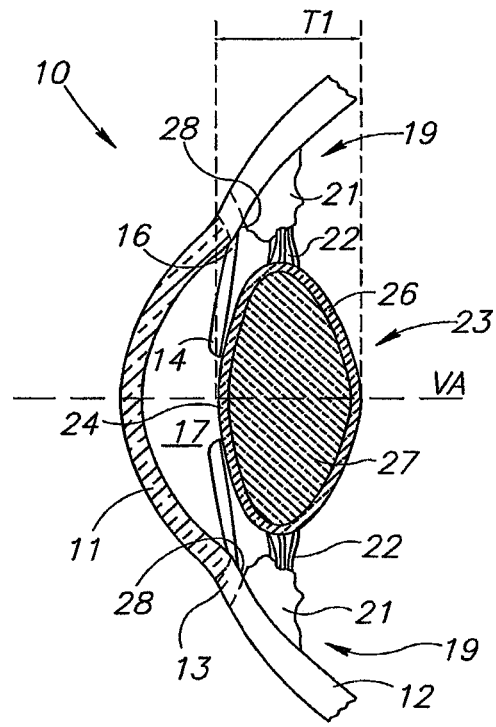
FIG. 1 is a cross section view of an anterior part of a human eye in its natural near vision condition in an axial plane of the human body.
Figure 2:
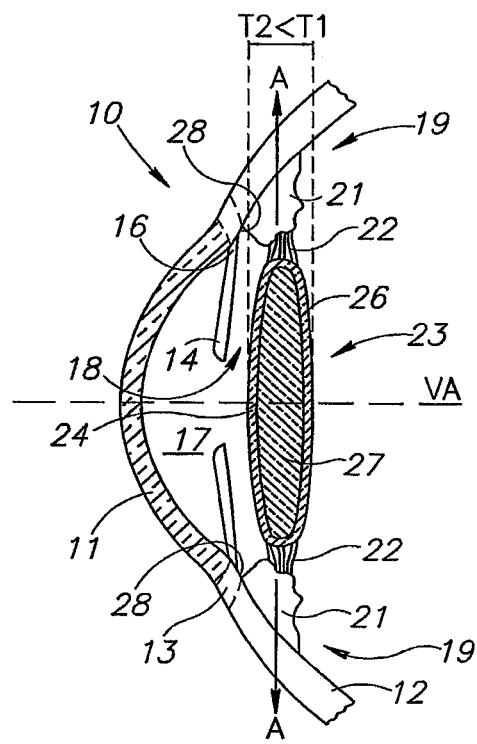
FIG. 2 is a cross section view of an anterior part of a human eye in its natural distance vision condition in an axial plane of the human body.

FIGS. 1 and 2 are cross section views of an anterior part of a human eye 10 having a visual axis VA in its natural near and distance vision conditions, respectively, in an axial plane of the human body. The human eye 10 has a cornea 11 peripherally connected to a spherical exterior body made of tough connective tissue known as the sclera 12 at an annular sclero-corneal juncture 13. An iris 14 inwardly extends into the human eye 10 from its root 16 at the sclero-corneal juncture 13 to divide the human eye's anterior part into an anterior chamber 17 and a posterior chamber 18. A sphincter-like peripheral structure known as the ciliary body 19 includes ciliary processes housing ciliary muscles 21 fired by parasympathetic nerves. The ciliary muscles 21 are connected to zonular fibers 22 which in turn are peripherally connected to the equatorial edge of a membrane known as the capsular bag 23 with an anterior capsule 24 and a posterior capsule 26 enrobing a natural crystalline lens 27. The iris's root 16 and the ciliary body 19 delimit a portion of the interior surface of the sclera 12 at the sclero-corneal juncture 13 known as the ciliary sulcus 28. Remnants of the anterior capsule 24 which may remain after extraction of the natural crystalline lens 27 and the intact posterior capsule 26 are referred to hereinafter as the capsular diaphragm 29. Contraction of the ciliary body 19 allows the lens 27 to thicken to its natural thickness T1 along the visual axis VA for greater positive optical power for near vision (see FIG. 1). Relaxation of the ciliary body 19 tensions the zonular fibers 22 which draws the capsular bag 23 radially outward as shown by arrows A for compressing the lens 27 to shorten its thickness along the visual axis VA to T2<T1 for lower positive optical power for distance vision (see FIG. 2).

FIGS. 3-5 show a two part AIOL assembly 31 made from suitable bio-compatible material such as PMMA, and including a haptics system 32 for self-anchoring implantation in a human eye's ciliary sulcus 28 for retaining an AIOL 33 therein for enabling spectacle free vision over the nominal range of human vision. The haptics system 32 includes a tubular main body 34 with an axial length L1 along a longitudinal axis 36 (see FIG. 6), and a pair of diametrically opposite haptics 37 tangentially extending therefrom in opposite directions in a front view of the haptics system 32. The haptics 37 have a pair of parallel and opposite attachment plates 38 with pointed penetrating members 39 of sufficient strength for forced penetration into the tough connective tissue of a human eye's sclera 12. The penetrating members 39 are preferably dimensioned so as to penetrate slightly more than half of a sclera's thickness of about 1 mm.

The main body 34 is in the form of a flexible split ring 41 with a male end 42 for releasable interference fit into a complementary female end 43 such that the main body 34 is capable of assuming a clamping state for tightly clamping the AIOL 33 therein. The male end 42 and the female end 43 are each provided with an axially directed bore 44 such that the split ring 41 can be prized apart by a suitable ophthalmic surgical tool (not shown) to an unclamping state for enabling axial displacement of the AIOL 33 for positioning purposes for compensating for capsular contraction, its entire replacement if necessary, and the like.

The haptics 37 have a thin profile in a plane perpendicular to the longitudinal axis 36 such that they are sufficiently flexible for encircling around the main body 34 in a direction shown by arrow C for facilitating insertion of the haptics system 32 through a relatively small incision into a human eye. FIG. 4 includes a haptics 37 in dotted lines for showing its encircling around the main body 34. The haptics 37 have a wide profile along the longitudinal axis 36 such that they are rigid against a compressive force therealong. The wide profile preferably tapers from a haptics' proximal end 37A adjacent the main body 34 towards its distal end 37B remote therefrom.

The AIOL 33 includes a tubular casing 47 with an axial length L2 along a longitudinal axis 48, a leading optically clear aperture lens 49 with an anterior surface 51, and a trailing flange 52. The casing's axial length L2 is longer than the main body's axial length L1 such that the main body 34 is capable of fully contacting the casing 47 along an adjustment stroke longer than the main body's axial length L1. The casing 47 slidingly supports a tubular piston-like member 53 with a leading flange 54 and a trailing flange 56 acting as a posterior surface against which a human eye's capsular diaphragm 29 bears. The AIOL 33 houses a shape memory optical element 57 made from soft gel or a fluid or gas filled membrane. The soft gel or fluid may be silicone based or water based, for example, Balanced Salt Solution (BSS), or any other biocompatible transparent liquid having a refractive index similar to that of the natural crystalline lens 27 or greater. The AIOL 33 includes a flange 58 for abutting against the main body 34 to stop displacement of the AIOL 33 in a posterior direction.

The optical element 57 has a natural disc shape with a natural low Diopter strength for distance vision purposes and which urges the piston-like member 53 to a natural extended position (see FIG. 6). The optical element 57 is capable of being resiliently elastically deformed to a deformed shape by a force imparted by a human eye's capsular diaphragm on relaxation of its ciliary body acting against the piston-like member 53 in an anterior direction such that the piston-like member 53 assumes a compressed position with some of the optical element 57 bulging thereinto for rendering a high Diopter strength for near vision purposes (see FIG. 7). The piston-like member 53 is urged from its compressed position outwards to its natural extended position by the optical element 57 reverting to its natural shape on constriction of a human eye's ciliary body. Thus, the AIOL has a continuous variable Diopter strength between a minimum Diopter strength suitable for distance vision purposes and a maximum Diopter strength suitable for near vision purposes depending on the degree of compression of the piston-like member 53 in the casing 47.

FIG. 8 shows an AIOL 61 also suitable for deployment in the haptics system 32 for correcting human eyesight. The AIOL 61 includes a tubular casing 62 with a longitudinal axis 63, and a flat aperture lens 64 constituting an anterior surface and having a central aperture 66. The casing 62 houses a shape memory optical element 67 of a natural disc shape, and a semi-spherical transparent piston-like member 68 having a flat surface 69 juxtaposed against the optical element 67 and a convex shaped posterior surface 71 against which a human eye's capsular diaphragm 29 directly bears for affecting the AIOL's Diopter strength. The optical element 67 has a natural low Diopter strength and is capable of being resiliently elastically deformed to a deformed shape with some of it bulging through the central aperture 66 on relaxation of a human eye's ciliary body for increasing the AIOL's Diopter strength.

FIG. 9 shows an AIOL 81 also suitable for deployment in the haptics system 32 for correcting eyesight. The AIOL 81 includes a tubular casing 82 with a longitudinal axis 83, and a plano-convex aperture lens 84 constituting an anterior surface. The casing 82 houses a shape memory optical element 86 with a natural spherical shape and a posterior surface 87 against which a human eye's capsular diaphragm 29 directly bears for affecting the AIOL's Diopter strength. The optical element 86 has a natural high Diopter strength and is capable of being resiliently elastically deformed to a compressed shape on relaxation of a human eye's ciliary body urging its capsular diaphragm 29 against the posterior surface 87 in an anterior direction for decreasing the AIOL's Diopter strength in a similar fashion as the natural crystalline lens 27.

Figure 10:
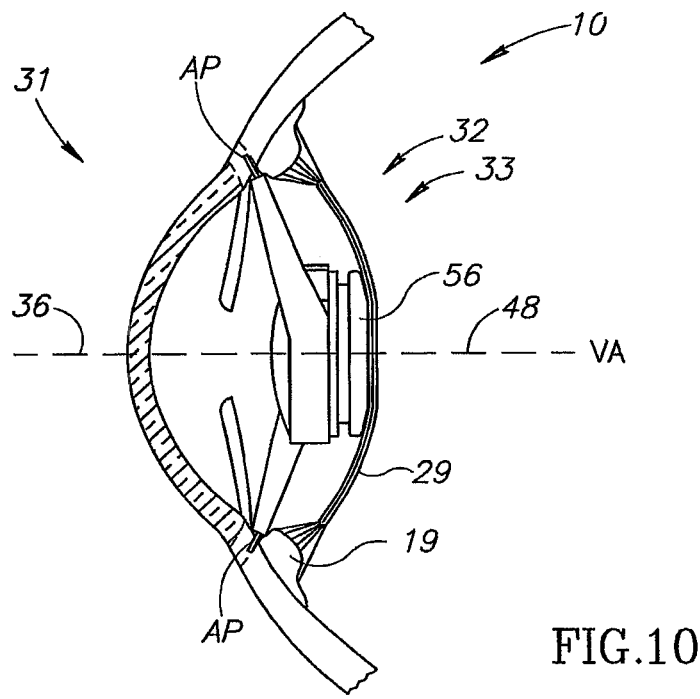
FIG. 10 is a cross section view of an anterior part of a human eye showing an initial position of FIG. 3's AIOL assembly along the human eye's visual axis in an axial plane of the human body.
Figure 11:
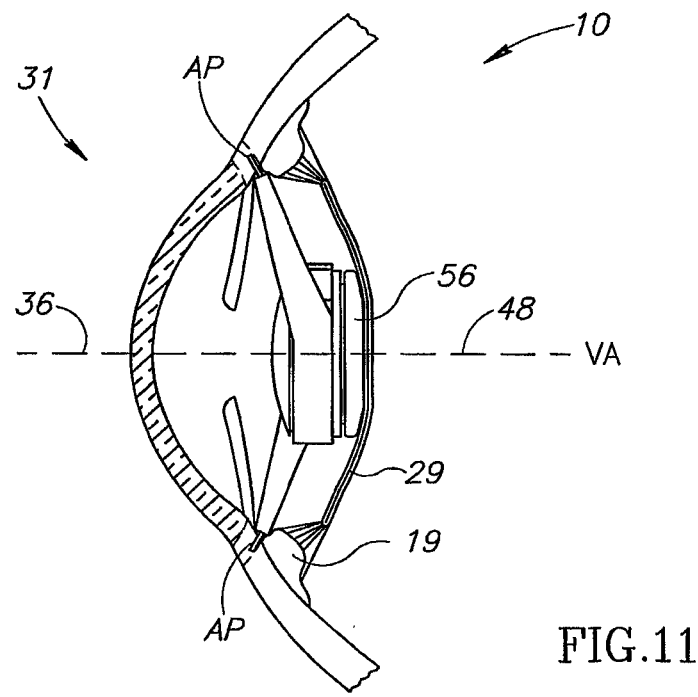
FIG. 11 is a cross section view of an anterior part of a human eye showing a subsequent position of FIG. 3's AIOL assembly along the human eye's visual axis for compensating for capsular contraction in an axial plane of the human body.
Figure 12:
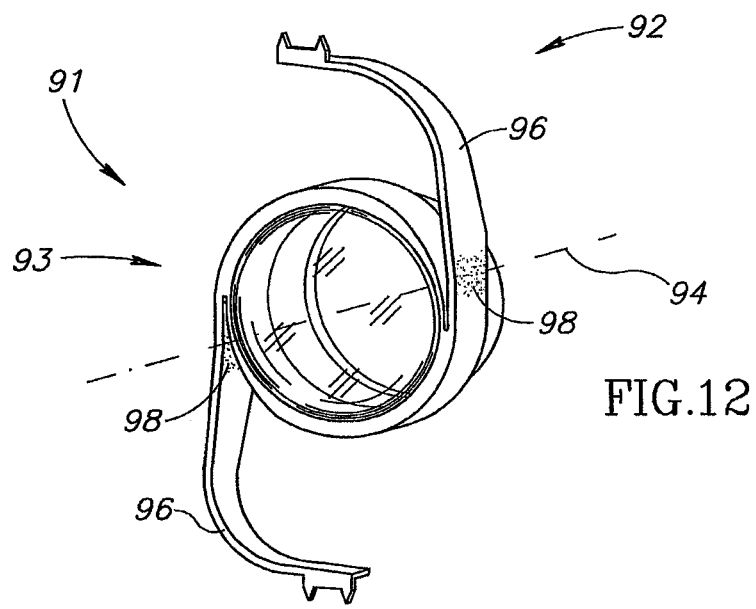
FIG. 12 is a perspective view of a unitary AIOL assembly in accordance with the present invention.
Figure 13:
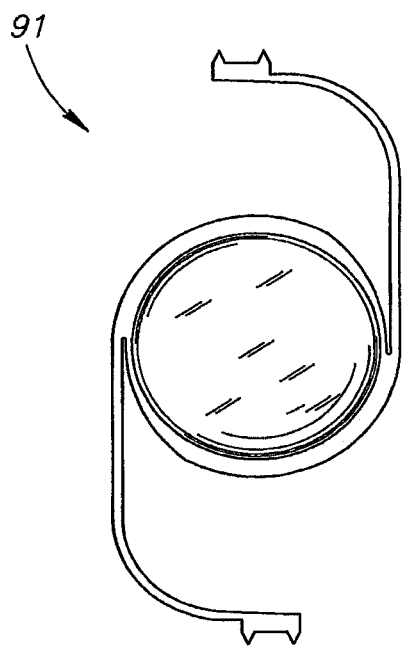
FIG. 13 is a front view of FIG. 12's AIOL assembly.
Figure 14:
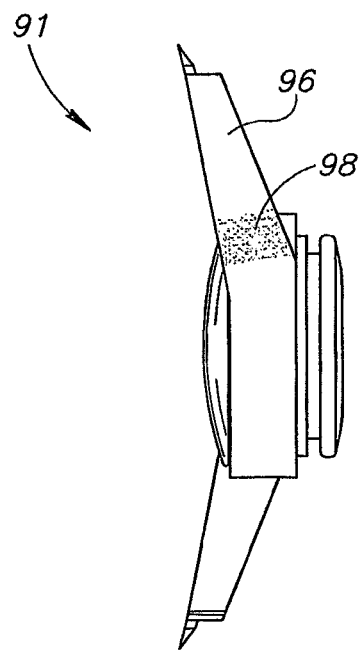
FIG. 14 is a side view of FIG. 12's AIOL assembly.
Figure 15:
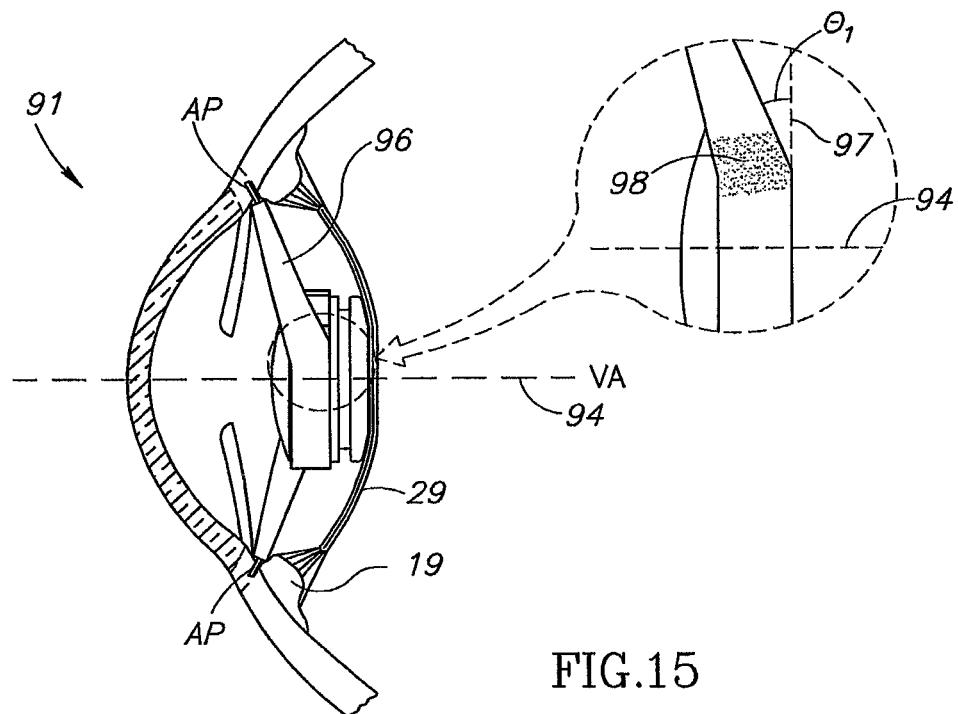
FIG. 15 is a cross section view of an anterior part of a human eye showing an initial position of FIG. 12's AIOL assembly along the human eye's visual axis in an axial plane of the human body.
Figure 16:
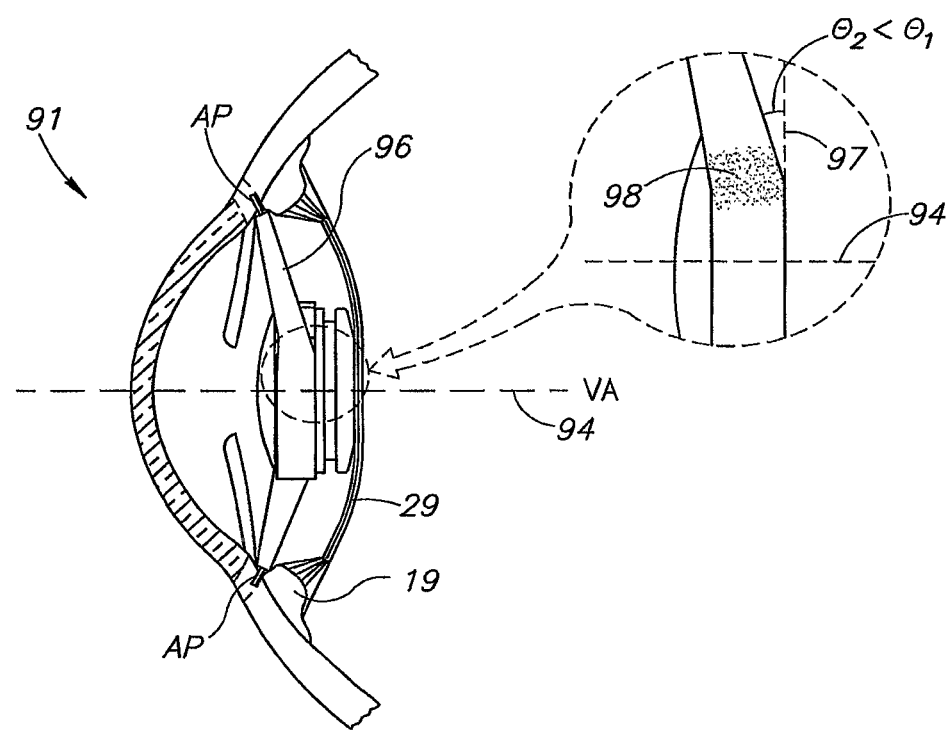
FIG. 16 is a cross section view of an anterior part of a human eye showing a subsequent position of FIG. 12's AIOL assembly along the human eye's visual axis for compensating for capsular contraction in an axial plane of the human body.

The implantation of an AIOL assembly of a variable Diopter strength in a human eye 10 after removal of its natural crystalline lens 27 is now described in connection with the AIOL assembly 31 with reference to FIGS. 10 and 11. The AIOL assembly 31 is set up such that the AIOL's longitudinal axis 48 coincides with the haptics system's longitudinal axis 36 and the annular flange 58 abuts against the main body 34 as shown in FIG. 6. The AIOL assembly 31 is typically implanted into a human eye 10 after administration of a suitable muscle relaxant for relaxing both its ciliary muscles and its iris muscles thereby dilating its pupil. The capsular diaphragm 29 has some slack by virtue of the removal of the natural crystalline lens 27. FIG. 10 shows that the haptics system's puncturing members 39 are forcibly inserted into the sclera 12 at stationary anchor points AP for retaining the AIOL assembly 31 in the annular ciliary sulcus 28. FIG. 10 also shows that the AIOL assembly 31 is deployed such that its longitudinal axes 36 and 48 are co-directional and preferably co-axial with the visual axis VA and the trailing flange 56 is urged in a posterior direction against the capsular diaphragm 29 tensioning same to become sufficiently taut to urge the AIOL 33 to its extreme compressed position as shown in FIG. 7 with maximum Diopter strength suitable for near vision purposes. Constriction of the ciliary body 19 enables the AIOL 33 to assume its extreme extended position as shown in FIG. 6 with minimum Diopter strength suitable for distance vision purposes. In the case of capsular contraction, the AIOL 33 is unable to assume its extreme extended position but rather it remains at least partially compressed depending on the degree of the capsular contraction thereby diminishing its accommodation ability. The accommodation ability of the AIOL 33 is restored by prizing open the split ring 41 and moving the AIOL 33 in an anterior direction as evidenced by the gap between the AIOL's flange 58 and the split ring 41 as seen in FIG. 11.

FIGS. 12-16 show an AIOL assembly 91 which is similar to the AIOL assembly 31 but differs therefrom in two respects: First, the AIOL assembly 91 is unitary insofar that it includes a haptics system 92 for self-anchoring implantation in a human eye's ciliary sulcus 28 at at least two stationary anchor points AP integrally formed with an AIOL 93 of variable Diopter strength. And second, the haptics system 92 has a longitudinal axis 94 and includes a pair of haptics 96 which are capable of being plastically deformed from an initial acute angle θ1 (see FIG. 15) subtended with respect to a plane 97 perpendicular to the longitudinal axis 94 to a less acute angle θ2<θ1 (see FIG. 16) such that the haptics system 92 is capable of in situ selective displacement of the AIOL 93 from an initial position to a desired position along a human eye's visual axis VA. This is achieved by the haptics 96 having regions 98 adjacent the AIOL 93 impregnated with radiation sensitive bio-compatible chemicals, for example, Infra Red (IR) sensitive indocyanine green (ICG), and the like, such that the haptics 96 are plastically deformable on heating to a so-called glass transmission temperature higher than a human eye's normal 36° ° C. temperature but sufficiently low so as to not damage a human eye's delicate internal structures.

Figure 17:
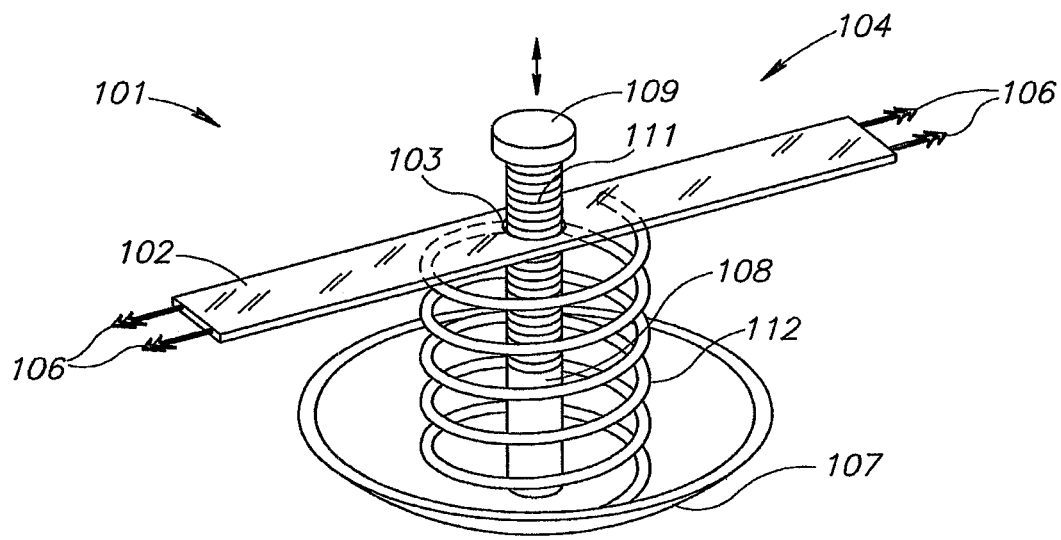
FIG. 17 is a perspective view of an accommodation measurement implant for measuring accommodation and accommodation forces in an experimental set-up including an animal eye.
Figure 18:
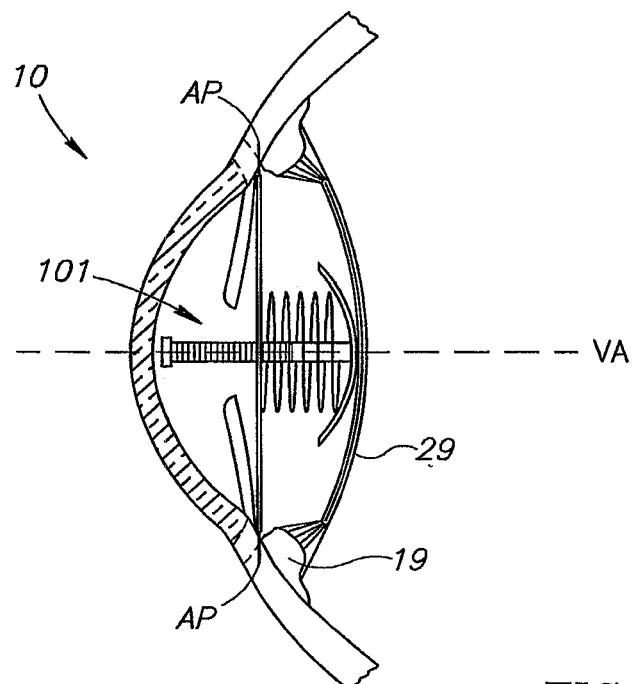
FIG. 18 is a cross section view showing deployment of the accommodation measurement implant of FIG. 17.

FIGS. 17 and 18 show an accommodation measurement implant (AMI) 101 for determining accommodation and accommodation forces in an experimental set-up including an animal eye similar to a human eye and therefore likewise numbered. The AMI 101 includes a generally rectangular rigid planar base member 102, and a central aperture 103. The base member 102 includes a haptics system 104 in the form of oppositely directed pointed puncturing members 106 for self-anchoring at anchor points AP. A convex shaped member 107 suitably shaped and dimensioned for placing on an animal eye's capsular diaphragm 29 from the anterior direction is provided with an upright pin 108 having a pinhead 109 and passing through the aperture 103. The pin 108 includes a series of graduations 111 therealong at a pitch of less than 500 μm, and preferably at 250 μm. A helical compression spring 112 is placed between the base member 102 and the convex shaped member 207 for urging them apart to be stopped by the pinhead 109 abutting against the base member 102. The base member 102, the convex shaped member 107, and the pin 108 are preferably formed of a suitable biocompatible material, for example, stainless steel, PMMA, and the like. Accommodation is determined as a function of a pin's displacement relative to the base member 102 as a result of relaxation of the ciliary body 19. Pin displacements may be detected by external devices or alternatively the graduations 111 may be inspected by a direct eye inspection. The actual forces developed by the relaxation of a ciliary body can be determined as a function of the compression spring's spring constant k and pin displacement.

While the invention has been described with respect to a limited number of embodiments, it will be appreciated that many variations, modifications, and other applications of the invention can be made within the scope of the appended claims.

What is claimed is:

1. An accommodating intraocular lens (AIOL) comprising:
   an optical element containing a liquid, the optical element comprising an anterior-facing surface configured to be resiliently deformed to increase diopter strength of the optical element upon application of a compressive force against the optical element, wherein upon implantation of the AIOL in an eye, a visual axis of the eye extends through a central region of the anterior-facing surface and the anterior-facing surface forms an external surface of the accommodating intraocular lens;
   a reciprocating member operatively coupled to the optical element, the reciprocating member comprising a trailing end and an opposite leading end, wherein upon implantation of the AIOL in the eye, the reciprocating member is reversibly movable in response to accommodative eye movements such that the trailing end of the reciprocating member is configured to contact eye tissue driving shape change of the AIOL so that the leading end of the reciprocating member is urged against the optical element to resiliently deform the anterior-facing surface outward due to application of the compressive force against the optical element by the leading end of the reciprocating member, thereby causing the increase in diopter strength; and
   a haptics system coupled to and extending outward from the optical element.

2. The accommodating intraocular lens of claim 1, wherein the haptics system comprises at least two haptics, each of the at least two haptics comprising a penetrating member.

3. The accommodating intraocular lens of claim 1, whereby the reciprocating member is movable from a posterior direction to an anterior direction along the visual axis of the eye.

4. The accommodating intraocular lens of claim 1, wherein the AIOL has a first Diopter strength for distance vision purposes at rest and upon deformation of the anterior-facing surface outward to a shape with a second Diopter strength higher than the first Diopter strength.

5. The accommodating intraocular lens of claim 1, wherein the optical element further comprises an outer main body that is a ring having an axial length along a longitudinal axis, the ring surrounding an axial length of the optical element such that at least a portion of the optical element is contained by the main body.

6. The accommodating intraocular lens of claim 1, wherein the liquid of the optical element comprises a silicone-based or water-based liquid.

7. The accommodating intraocular lens of claim 6, further comprising a second optical element supported by an outer main body and optically aligned with the optical element.

8. The accommodating intraocular lens of claim 1, wherein the haptics system forms at least two spaced apart, stationary anchor points upon implantation of the AIOL in the eye adapted to retain the AIOL in the eye.

* * * * *